United States Patent
Axelsson et al.

(10) Patent No.: US 8,138,332 B2
(45) Date of Patent: Mar. 20, 2012

(54) SYNTHESIS OF CYCLEN DERIVATIVES

(75) Inventors: Oskar Axelsson, Hagan (NO); Andreas Olsson, Malmo (SE)

(73) Assignee: GE Healthcare AS, Oslo (NO)

( * ) Notice: Subject to any disclaimer, the term of this patent is extended or adjusted under 35 U.S.C. 154(b) by 657 days.

(21) Appl. No.: 11/911,848

(22) PCT Filed: Apr. 18, 2006

(86) PCT No.: PCT/NO2006/000141
§ 371 (c)(1),
(2), (4) Date: Apr. 2, 2009

(87) PCT Pub. No.: WO2006/112723
PCT Pub. Date: Oct. 26, 2006

(65) Prior Publication Data
US 2009/0216011 A1      Aug. 27, 2009

(30) Foreign Application Priority Data
Apr. 19, 2005   (NO) .................................. 20051911

(51) Int. Cl.
*C07D 257/02* (2006.01)

(52) U.S. Cl. ....................................................... 540/474
(58) Field of Classification Search .................. None
See application file for complete search history.

(56) References Cited

FOREIGN PATENT DOCUMENTS

| WO | 93/02045 | 2/1993 |
| WO | 95/09848 | 4/1995 |

OTHER PUBLICATIONS

PCT/NO2006/000141 International Search Report/Written Opinion dated Aug. 4, 2006.
Dadabhoy "Long wavelength sensitizers for europium (III) luminescence on acridone derivatives" Journal of the Chemical society, Perkin Transactions 2., vol. 2, 2002, pp. 348-357, GB Chemical society, Letchworth.

*Primary Examiner* — Noble Jarrell

(57) ABSTRACT

The invention relates to an improved process for preparation of protected DO3A, such as DO3A-tri-t-butyl ester (1,4,7,10-tetraazacyclododecane-1,4,7-triacetic acid tri-t-butyl ester). The compound is prepared as a salt. The process includes a work-up procedure giving DO3A-tri-t-butyl ester as a salt of excellent purity.

14 Claims, No Drawings

SYNTHESIS OF CYCLEN DERIVATIVES

FIELD OF THE INVENTION

This application is a filing under 35 U.S.C. 371 of international application number PCT/NO2006/000141, filed Apr. 18, 2006, which claims priority to application number 20051911 filed Apr. 19, 2005, in Norway the entire disclosure of which is hereby incorporated by reference.

The invention relates to a process for the preparation of salts of protected DO3A, such as salts of DO3A-tri-t-butyl ester.

BACKGROUND OF INVENTION

Magnetic Resonance Imaging (MRI) is a well-established and powerful technique for studying the internal structure of the human body. In the field of MRI, various lanthanide chelates of cyclen-based macrocyclic chelating agents have been proposed as contrast agents. Such macrocyclic chelating agents form particularly stable chelate complexes with the contrast-generating paramagnetic metal ions, such as gadolinium or dysprosium, and thus are suitable carriers for the metal ions to ensure appropriate biodistribution and elimination.

Cyclen (1,4,7,10-tetraazacyclododecane) is a key compound in the preparation of many of these macrocyclic chelants. The group of tri-N-alkylated cyclens constitutes another important group of compounds for the preparation of such macrocyclic chelants. DO3A (1,4,7,10-tetraazacyclododecane-N,N',N''-triacetic acid) is one such tri-N-alkylated cyclen compound that forms basis for Magnetic Resonance (MR) contrast agents. A group of related compounds is the protected forms of the DO3A compound, such as DO3A-tri-t-butyl ester (1,4,7,10-tetraazacyclododecane-1,4,7-triacetic acid tri-t-butyl ester), wherein the three carboxyl groups are protected.

Protected DO3A compounds, such as DO3A-tri-t-butyl ester, and the salts thereof, are valuable intermediates in the preparation of MR contrast agents based on DO3A, such as e.g. Gd(HP-DO3A) (ProHance™), and Gd(DO3A-butrol) (Gadovist™).

DO3A-tri-t-butyl ester is a commercially available product, but in addition to being expensive the commercially available products contain impurities of both the di-alkylated and tetra-alkylated cyclen. Some methods for preparation of the compound are known from the prior art.

U.S. Pat. No. 5,419,893 is directed to chelating agents, such as cyclene based compounds, and the preparation thereof. A preparation of DO3A-tri-t-butyl ester from cyclen and t-butylbromo acetate is presented. The preparation includes purification by flash chromatography. The products are prepared as free bases.

WO 2005/003105 presents a method of preparing tri-alkylated 1,4,7,10-tetraazacyclododecanes by reaction of cyclen and appropriate electrophiles. The reaction takes place in an aprotic solvent such as chloroform. The product is purified by column chromatography. The products are prepared as free bases.

As noted above, DO3A-tri-t-butyl ester is an important starting material for the preparation of macrocyclic chelating agents and MR contrast agents. Commercially available DO3A-tri-t-butyl ester is expensive and comprises impurities. Existing synthetic routes require expensive and time consuming purification, such as chromatography, being a particular drawback when producing in large scale. A new process for preparation of DO3A-tri-tert-butyl ester, which is less expensive and which provides a product of improved purity is hence sought.

SUMMARY OF THE INVENTION

In view of the needs of the art the present invention provides an improved process for preparation of protected DO3A, such as DO3A-tri-t-butyl ester (1,4,7,10-tetraazacyclododecane-1,4,7-triacetic acid tri-t-butyl ester). The compounds are prepared as salts. The process includes a work-up procedure providing DO3A-tri-t-butyl ester as a salt of improved purity.

DETAILED DESCRIPTION OF THE INVENTION

Viewed from one aspect the invention provides a process for preparation of a protected DO3A salt of formula I,

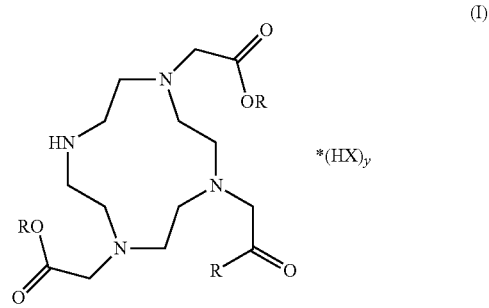

(I)

wherein R represents a carboxyl protective group, e.g. selected from the group of alkyls, such as $C_1$-$C_6$ alkyls, aryls and substituted aryls. Methyl, propyl, benzyl and t-butyl are preferred R-groups. Most preferably R is t-butyl. X represents a chlorine, bromine or iodine anion or a sulphonate- or phosphate-containing group, and is preferably a bromine anion. y represents an integer of from 1 to 4 and is preferably 1.

When X comprises a phosphate group the salt formed is based on a phosphoric acid ($H_3PO_4$), phosphonic acid ($R'PO_3H_2$) or a phosphinic acid ($R'R''PO_2H$), wherein R' and R'' are lower alkyl groups, such as a $C_1$-$C_6$ alkyl. When X comprises a sulphonate group this group may further include a lower alkyl group, such as $C_1$-$C_6$ alkyl, e.g. forming the methyl-$SO_3H$ salt.

Viewed from a preferred embodiment the invention provides a process for preparation of DO3A-tri-t-butyl ester, of formula II, as a salt.

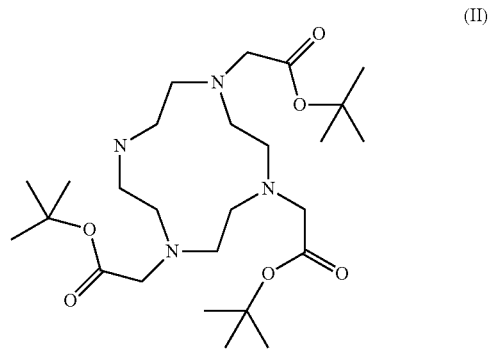

(II)

More preferably, the invention provides a process for preparation of a mono salt of the compounds of formula I, such as the HBr salt of DO3A-tri-t-butyl ester (4,7-bis-tert-butoxycarbonylmethyl-1,4,7,10-tetraaza-cyclododec-1-yl)-acetic acid tert-butyl ester hydrobromide).

The process for the preparation of compounds of formula (I) according to the invention provides a new work-up procedure involving an optimised precipitation providing material of high purity and in high yields. The new work-up procedure selectively provides high yields of the tri-N-alkylated product as a salt. It has been found that it is much simpler to prepare protected DO3A of formula I, such as DO3A-tri-t-butyl ester, of high purity when preparing this as a salt, compared to preparations of the free base. Obtaining the tri-N-alkylated product in pure form is found to be greatly increased when precipitating the product in its salt form. A great advantage of the process of the invention is that the salt of tri-alkylated product can be separated from by-products by precipitation and that no, or minimal, further purification of the precipitated salt end product is needed. The simple process is especially beneficial when producing the product in large quantities.

All starting materials, solvents and auxiliaries, such as bases, are commercially available. The procedure is easy to perform and no special reagents or harsh reaction conditions are required.

In a first embodiment the invention provides a process for the preparation of compounds of formula I comprising the steps:
(1) reacting cyclen and an alkylation agent being an activated acetic acid ester to form a mixture, the mixture comprising protected DO3A;
(2) adjusting the pH of the mixture to 9.0±0.5;
(3) adding a salt to the mixture;
(4) collecting the precipitated product.

The steps may be carried out in the order as given, or alternatively, the order of step (2) and (3) may be changed, such that the addition of the salt (3) is carried out prior to adjusting the pH (2). The steps are preferably carried out in the order as given. All steps are further outlined below.

After the pH adjustment and the addition of the salt, a crystalline material starts precipitating. The process further comprises optional steps accelerating and completing the precipitation in addition to collecting and drying the precipitate, to obtain a salt of protected DO3A of formula (I) of high purity and in a high yield. The selective precipitation of the tri-alkylated product of formula (I) is a result of the combination of optimising the alkylation in step (1) and adjusting the pH in step (2).

Step (1) comprises reacting 1,4,7,10-tetraazacyclododecane (cyclen) of formula (III)

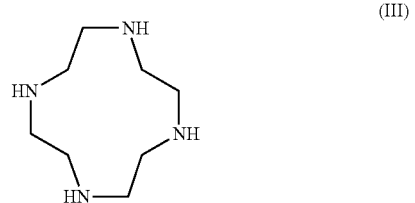

with an activated acetic acid ester of formula (IV), acting as an alkylation agent,

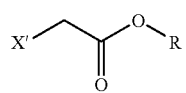

(IV) wherein X' is a readily displaceable group selected from the group of chlorine, bromine, iodine, sulphonates, and phosphates. Preferably X' is bromine. R is a carboxyl protective group selected from the group of alkyls, such as $C_1$-$C_6$ alkyls, aryls and substituted aryls. Methyl, propyl, benzyl and t-butyl are preferred R-groups. More preferably R is t-butyl. Most preferably the alkylation agent of formula IV is tert-butylbromo acetate of formula (V).

The reaction of step (1) is carried out in the presence of a solvent. To optimise the alkylation step, the alkylation agent is dissolved in a water-miscible, polar solvent e.g. comprising amide, nitrile, ketone or alcohol groups. Preferably the solvent is N,N-dimethylacetamide. A suspension of cyclen and an auxiliary weak base, in a water-miscible, polar solvent is prepared. The solvent for cyclen is preferably the same solvent as used for the alkylation agent, i.e. preferably N,N-dimethylacetamide. The weak base is e.g triethylamine or sodium acetate. The role of the base is to remove cyclen protons. The solution of the alkylation agent is added to the suspension of cyclen, preferably drop wise under stirring.

The amounts of the components are selected in amounts sufficient to trialkylate the cyclen. The ratio between the reaction components in step (1) is preferably about 3 molar equivalents of the alkylation agent, 3 molar equivalents weak base to one molar equivalent cyclen. Reference is made to examples 1 and 2 for further details of appropriate amounts of the reactants, solvents and auxiliaries.

Following the addition of the alkylation agent the reaction vessel comprising the reaction mixture of step (1) is sealed and the suspension is preferably left until the reaction is completed, usually for several days, such as 1-8 days, e.g. 3-5 days. 3 days have been found to be sufficient for preparation of a salt of DO3A-tri-t-butyl ester. The reaction suspension is kept under stirring for this period.

The reaction of step (1) can be carried out within a broad temperature range, e.g. at a temperature between 0-30° C. During the addition of the alkylation agent to cyclen the temperature is preferably held between 0-10° C., e.g. between 0-5° C. When the addition of the alkylation agent is completed the temperature of the reaction suspension is preferably raised to about ambient temperature, e.g. to a temperature between 18-30° C., more preferably to a temperature between 20-25° C., and is kept at this temperature level during the completion of the reaction. If the temperature is increased significantly above this level, over-alkylation becomes more frequent and impurities such as tetra-alkylated products are more likely to be produced. Using the process of the invention the amounts of tetra-alkylated product generated in step (1) is kept at a minimum level. Especially in a large scale procedure it is advised to lower the temperature when performing the initial addition of the alkylation agent to avoid impurities of the tetra-alkylated product. The main product from the alkylation step (1) is the tri-alkylated cyclen of formula (I) in its non-salt form. The main by-product is the di-alkylated product. This by-product is however more soluble in the mixture of step (1) than the tri-alkylated product, and will not precipitate when adjusting pH and adding a salt in the next steps.

The mixture of step (1), which is a suspension or slurry, may be prepared under other conditions using different solvents and auxiliaries than outlined above, depending on which product of formula (I), of the non-salt form, is prepared. Alternative solvents may e.g. be chosen based on which carboxylprotective groups are used.

Following step (1) the reaction mixture of step (1) is optionally poured into water. The addition of water is preferred as this provides a homogenous clear solution. The amount of water is e.g. 1-10 times the volume of the reaction suspension, or more preferably 3-8 times the volume of the reaction suspension. The amount of water may beneficially be kept in the lower part of the suggested range when producing large quantities, as the main object is to obtain a homogenous solution. The temperature of the water is about ambient temperature, e.g. 18-30° C., or between 20-25° C.

In step (2), pH is adjusted to 9.0±0.5, preferably to 8.7-9.3, more preferably to 8.9-9.1 and most preferably to about 9.0, by addition of a base. The pKa values of the nitrogen molecules of mono-, di-, tri- and tetra-alkylated products are different. It has been found that optimisation of the pH to the provided range ensures separation of the tri-alkylated product from any lower or higher alkylated by-products present in the reaction mixture of step (1), as mono-, di-, tri- and tetra-alkylated products precipitate to different extents at a given pH. Any impurities of the more soluble di-alkylated product, which is the likely main by-product, is kept in the solution at the preferred pH as a result, and will not precipitate when preparing the salt end product. The base used is preferably added in its solid form and is selected from the group of sodium carbonate, sodium bicarbonate, potassium carbonate, potassium bicarbonate, alkali hydroxides or sodium phosphate. More preferred is addition of $NaHCO_3$ in solid form.

In step (3) a salt comprising an anion X is added to the mixture, such as to the solution of step (2), wherein X is selected from the group of chlorine, bromine and iodine anions, or a sulphonate- or phosphate-containing group, and is preferably a bromine anion. The sulphonate and phosphate groups may comprise a lower alkyl group, such as a $C_1$-$C_6$ alkyl chain. X is preferably the same moiety as X' in the activated acetic acid ester of formulas IV. The added salt is e.g. a potassium salt (i.e. KX), as potassium salts generally have a good stability. Most preferably KBr is added in step (3) and tert-butylbromo acetate is preferably used in step (1).

In one embodiment of the invention, step (3) comprises adding a salt to the mixture from step (1), prior to adjusting the pH (step (2)). In this embodiment, the reaction mixture of step (1) is preferably poured into water comprising the salt. The water has a temperature which enables dissolution of the salt or which allows for Ostwald ripening. The temperature of the water is e.g. 26-100° C., more preferably 40-100° C., and most preferably 45-55° C. A clear solution is preferably obtained. The benefits of the process of this embodiment is that step (4) comprising collecting the product will speed up, in that the filtration process is simplified due to preparation of larger particles.

The amount of salt added in step (3) is e.g. 0.3-4 times the molar amount of the alkylation agent in step (1), and is preferably 0.6-3 times the molar amount of the alkylation agent.

The salt is added to the mixture, preferably under stirring. A crystalline precipitate will start forming when both the pH has been adjusted and the salt is added. To obtain a rapid and complete precipitation step (4) preferably comprises an optional additional step adding a non-polar solvent, such as an ether, to the salt solution of step (3). The ether compound is preferably added when the salt added in step (3) is fully dissolved. The ether is e.g. selected from standard ethers such as lower alkyl ethers, dimethoxy ethane, diglyme, triglyme, THF, t-BuOMe, isopropyl ether and diethyl ether. More preferred is addition of diethyl ether. An amount of from about 10% to 20% by volume of the total solvent volume is appropriate. Addition of ether is found to improve both the yield on large scale synthesis and also increases the speed of precipitation of the polar salt.

Step (4) comprises the step of collecting the precipitated salt, e.g. by filtration or centrifugation, e.g. after 0.5-4 hours, for example after about 2 hours. Subsequently, the solvents used are removed from the collected product, preferably by evaporation, e.g. by evaporation at elevated temperature and/or reduced pressure (e.g. vacuum) to obtain the product in dry form.

Commercially available DO3A-tri-t-butyl ester contains some impurities of the tetra-alkylated cyclen (1,4,7,10-tetraaza-cyclododecane-tetraacetic acid tetra-t-butyl) and some di-alkylated cyclen (1,4,7,10-tetraaza-cyclododecane-diacetic acid di-t-butyl). The work-up procedure of the invention provides a salt of DO3A-tri-t-butyl ester of high purity. The work-up procedure as disclosed ensures that the desired tri-substituted product is separated from the reaction mixture, which may also include mono-, di- and tetra-substituted derivatives. The obtained product is, from standard levels of detection, free from the dialkylated product found in unwanted quantities in commercially available DO3A-tri-t-butyl ester. Any impurities of the tetra-alkylated product from step (1) do not precipitate as a salt. The purity of the product obtained may be controlled by various analytical methods like for instance NMR to confirm the structure and determine purity of the product, HPLC to determine purity and GC to determine residual solvents. The product prepared by the disclosed process, such as DO3A-tri-t-butyl ester HBr salt, has a purity of at least 95%, more preferably at least 99% and most preferably at least 99.9%.

The process of preparation according to the invention provides protected DO3A salt of formula (I) in good yield, preferably in a yield above 60% and more preferably above 70%, and most preferably above 80%, based on the molar amount of cyclen. Yields as high as 81.5% of DO3A-tri-t-butyl ester as the HBr salt have been achieved. A typical result is a yield of 73%.

Another aspect of the invention is compounds of formula I, as salts, a preferred compound being a salt of DO3A-tri-t-butyl ester, preferably the HBr mono salt.

Yet another aspect of the invention is compounds according to formula I prepared by the process as disclosed.

The protected DO3A, or the salt thereof, can be used in the preparation of DO3A by deprotecting the acetic acid groups. The protecting groups may be removed by standard techniques, for example hydrolysis, hydrogenolysis, etc. such as e.g. treating with trifluoroacetic acid or formic acid to give the free acids. DO3A, and derivatives, can be complexed with a paramagnetic metal atom and used as relaxation enhancement agents for magnetic resonance imaging. Alternatively, MR contrast agents, such as the commercially available product ProHance™, can be prepared from a salt of DO3A-tri-t-butyl ester, e.g. from the HBr salt, by involving an alkylation or epoxide opening step of DO3A-tri-t-butyl ester salt in the presence of a base, or alternatively by liberating the free base of the DO3A-tri-t-butyl ester in a separate step. The alkylation includes e.g. attaching a hydroxypropyl group at the reactive secondary amine. This may be followed by deprotection and finally complexation with $Gd^{3+}$ or another paramagnetic metal ion.

The present invention will now be further illustrated by way of the following non-limiting example.

EXAMPLES

Example 1

Preparation of the HBr salt of DO3A-tri-t-butyl ester

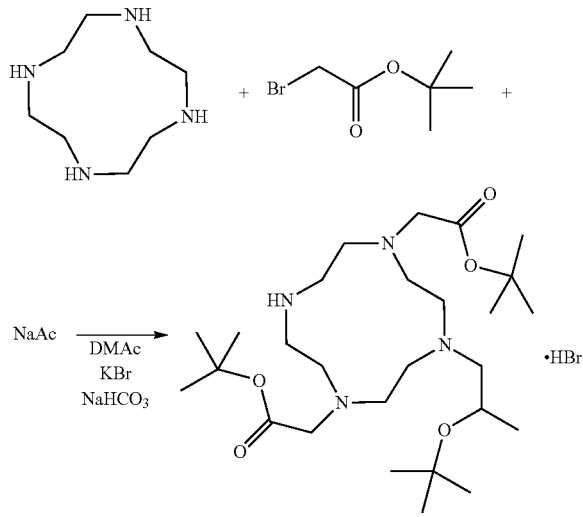

Tert-Butylbromo acetate (77.1 ml, 522 mmol) in N,N-dimethylacetamide (DMAc) (150 ml) was added dropwise to a stirred suspension of 1,4,7,10-tetraazacyclododecane (30 g, 174 mmol) and sodium acetate (NaAc) (42.9 g, 522 mmol) in N,N-dimethylacetamide (400 ml) at 0° C. over 25 min. After the last addition the reaction slurry was allowed to warm to room temperature. The reaction vessel was sealed with a glass stopper and the white suspension was left stirring for 5 days. The reaction slurry was poured out in water (2000 ml) to give a clear yellow solution.

The pH was adjusted to 9 by the addition of solid NaHCO$_3$. KBr (30.0 g, 252 mmol) was added under mechanical stirring and when the salt had dissolved fully, diethylether (10 ml) was added. After a few minutes a white crystalline material precipitated out. After one hour the precipitate was filtered off and dried in vacuum to give (4,7-bis-tert-butoxycarbonylmethyl-1,4,7,10-tetraaza-cyclododec-1-yl)-acetic acid tert-butyl ester hydrobromide as a white powder (77.3 g, 73%).

Anal. Calcd. for $C_{26}H_{53}BrN_4O_6$ C, 52.25%; H, 8.94; N, 9.37; O, 16.06. Found C, 52.2; H, 8.7; N, 9.0; O, 16.6.

Example 2

Alternative preparation of the HBr salt of DO3A-tri-t-butyl ester

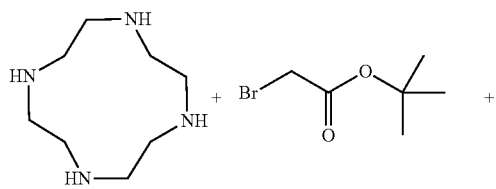

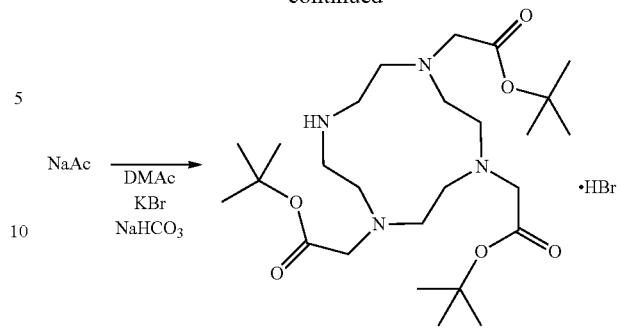

Tert-Butylbromo acetate (77.1 ml, 522 mmol) in N,N-dimethylacetamide (150 ml) was added dropwise to a stirred suspension of 1,4,7,10-tetraazacyclododecane (30 g, 174 mmol) and sodium acetate (42.9 g, 522 mmol) in N,N-dimethylacetamide (400 ml) at 0° C. over 25 min. After the last addition the reaction slurry was allowed to warm to room temperature. The reaction vessel was sealed with a glass stopper and the white suspension was left stirring for 5 days.

The reaction slurry was poured out in warm water (50° C., 2000 ml) containing dissolved KBr (30.0 g, 252 mmol), to give a clear yellow solution.

The pH was adjusted to 9 by the addition of solid NaHCO$_3$. After a few minutes a white crystalline material precipitated out. The slurry was allowed to cool to room temperature under slow stirring and then the precipitate was allowed to sediment without stirring over 4 hours. The precipitate was filtered off and dried in vacuum to give (4,7-bis-tert-butoxycarbonylmethyl-1,4,7,10-tetraaza-cyclododec-1-yl)-acetic acid tert-butyl ester hydrobromide as a white powder (77.3 g, 73%).

NMR results: DMSO-D$_6$ (400 MHz); 8.92 (2H), 3.41 (4H), 3.35 (2H), 2.98 (4H), 2.84 (4H), [2.71 (4H) 2.67 (4H)] Unresolved AB sys., 1.42 (27H)

What is claimed is:

1. A process for the preparation of compounds of formula (I)

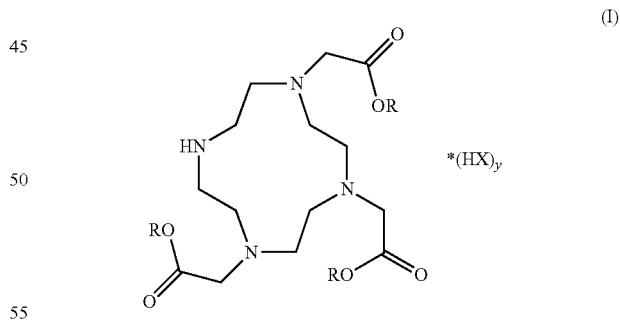

wherein R represents a carboxylprotective group selected from the group of alkyls, aryls, and substituted aryls;
X represents a chlorine, bromine or iodine anion or a sulphonate- or phosphate-containing group; and
y represents an integer of from 1 to 4; comprising the steps:
(1) reacting cyclen and an activated acetic acid ester to prepare a mixture;
(2) adjusting the pH of the mixture to 9.0±0.5;
(3) adding a salt to the mixture;
(4) collecting the precipitated product,
wherein step (3) is carried out prior to, or after, step (2).

2. A process as claimed in claim 1 wherein step (2) is carried out prior to step (3).

3. A process as claimed in claim 1 wherein step (3) is carried our prior to step (2).

4. A process as claimed in claim 1 wherein the activated acetic acid ester of step (1) is an alkylation agent of formula (IV),

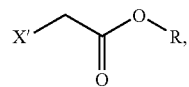
(IV)

wherein X' is a readily displaceable group selected from the group of chlorine, bromine, iodine, sulphonates and phosphates, and R is a carboxylprotective group selected from alkyls, aryls, and substituted aryls.

5. A process as claimed in claim 1 for the preparation of a compound of formula (I) wherein R represents t-butyl, X represents bromine and y is 1.

6. A process as claimed in claim 1 wherein step (1) is carried out in the presence of a water-miscible polar solvent.

7. A process as claimed in claim 6 wherein the solvent is N,N-dimethylacetamide.

8. A process as claimed in claim 1 wherein step (2) comprises adjusting pH by addition of sodium carbonate, sodium bicarbonate, potassium carbonate, potassium bicarbonate, alkali hydroxides or sodium phosphate.

9. A process as claimed in claim 1 wherein the salt added in step (3) comprises an anion X selected from the group of chlorine, bromine, iodine and a sulphonate- or phosphate-containing group.

10. A process as claimed in claim 1 wherein the salt added in step (3) is KBr.

11. A process as claimed in claim 1 wherein step (4) comprises adding a non-polar solvent to the mixture of step (3).

12. A process as claimed in claim 1 wherein step (4) comprises collecting the product by filtration or centrifugation followed by drying of the product.

13. A process as claimed in claim 1 wherein the obtained yield of the compound of formula (I) is above 60% based on the molar amount of the cyclen starting material.

14. A process as claimed in claim 1 providing a compound of formula (I) with a purity of at least 95%.

* * * * *